United States Patent [19]

Sarnoff et al.

[11] Patent Number: 4,578,064
[45] Date of Patent: Mar. 25, 1986

[54] PLURAL DOSAGE AUTOMATIC INJECTOR WITH IMPROVED SAFETY

[75] Inventors: Stanley J. Sarnoff; George B. Calkins; William R. Tarello, all of Bethesda, Md.

[73] Assignee: Survival Technology Inc., Bethesda, Md.

[21] Appl. No.: 563,768

[22] Filed: Dec. 21, 1983

[51] Int. Cl.⁴ .............................................. A61M 5/00
[52] U.S. Cl. .................................... 604/191; 604/137; 604/201
[58] Field of Search ............... 604/181, 187, 191, 196, 604/193, 194, 195, 95, 131, 156, 157, 192, 201, 218, 134–138

[56] References Cited

U.S. PATENT DOCUMENTS 4,226,235 10/1980 Sarnoff et al. ...................... 604/136
4,329,988 5/1982 Sarnoff et al. ...................... 604/137

Primary Examiner—C. Fred Rosenbaum
Assistant Examiner—Mark Rooney
Attorney, Agent, or Firm—Cushman, Darby & Cushman

[57] ABSTRACT

A plural dosage automatic injector comprising an elongated tubular housing assembly having side by side first and second medicament injecting assemblies each including a container, a hypodermic needle, a liquid medicament and a plunger within the forward end portion thereof and, first and second stressed spring assemblies in the rearward end portion thereof disposed in operative relation with said first and second medicament injecting assemblies for operating the latter. A manually operable safety device is provided which includes a first safety pin operable (1) when in a safety position with respect to the first spring stressed assembly to prevent actuation and release thereof and (2) when removed from its safety position to permit the actuation and release of the second stressed spring assembly. A mechanical motion transmitting mechanism is provided which is operable to transmit a movement occurring as a result of the actuation and release of the first stressed spring assembly into a secondary actuating movement operable to (1) effect a relative movement between the automatic safety pin and the second stressed spring assembly sufficient to remove the automatic safety pin from its safety position and (2) thereafter actuate and release second stressed spring assembly to operate the second medicament injecting assembly.

16 Claims, 4 Drawing Figures

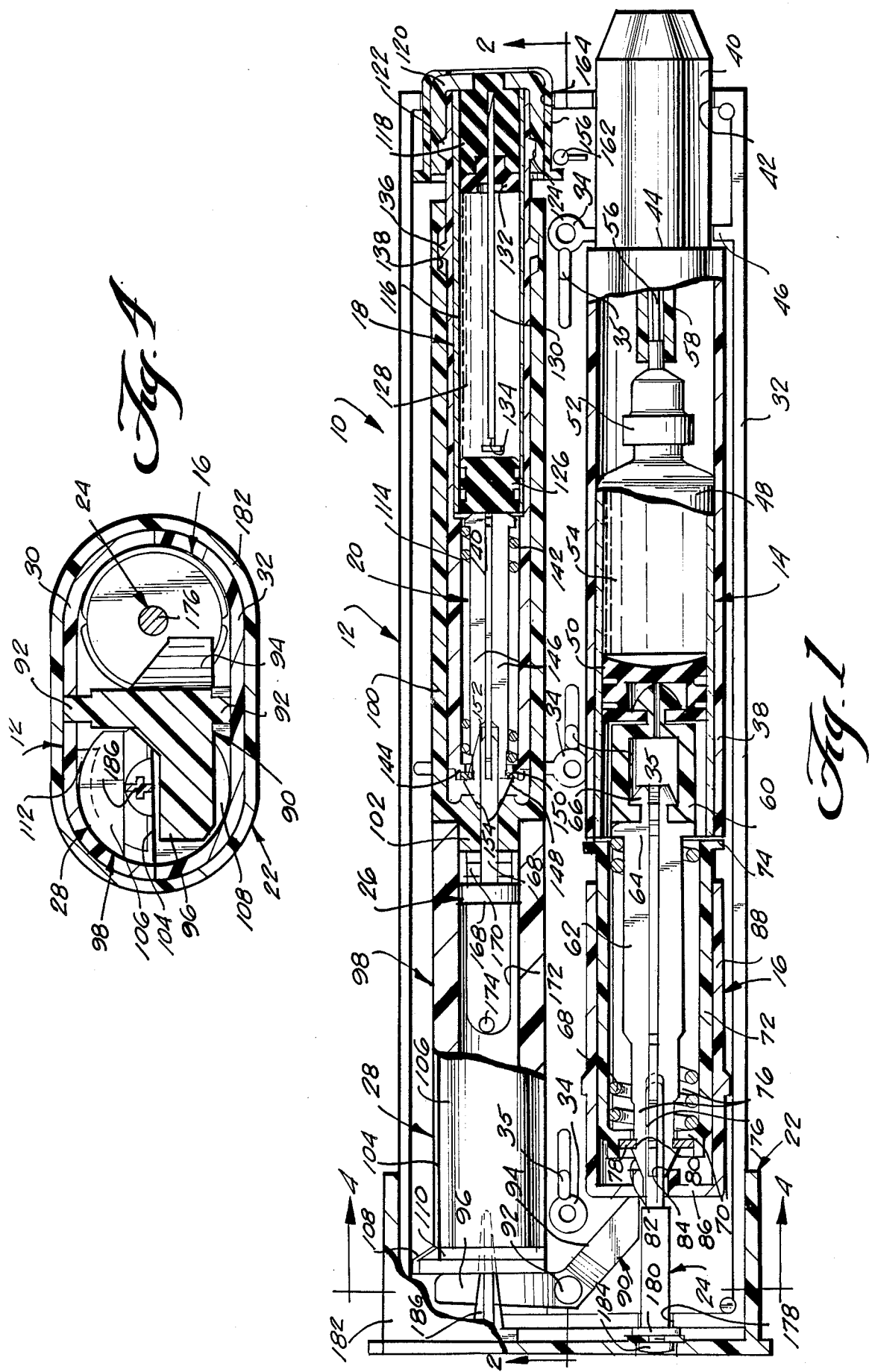

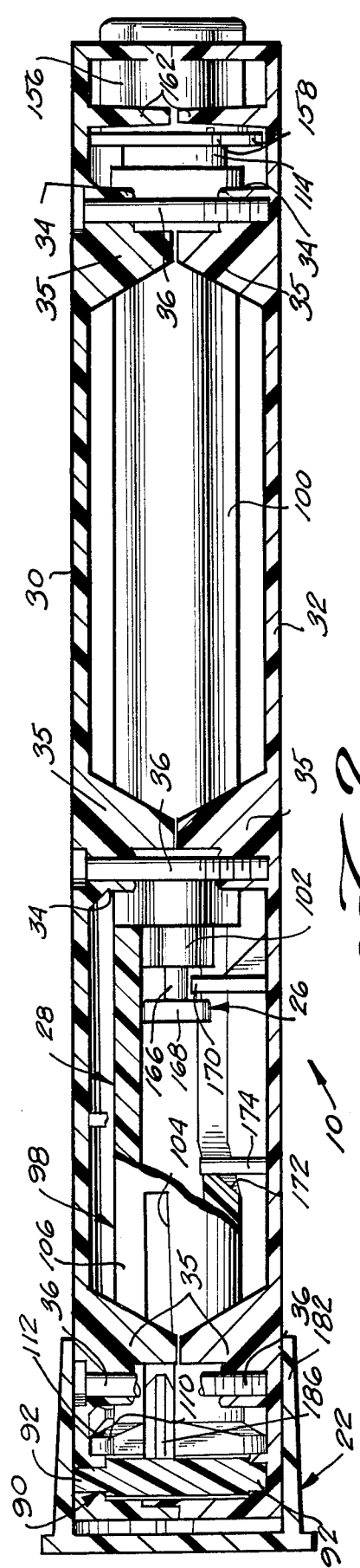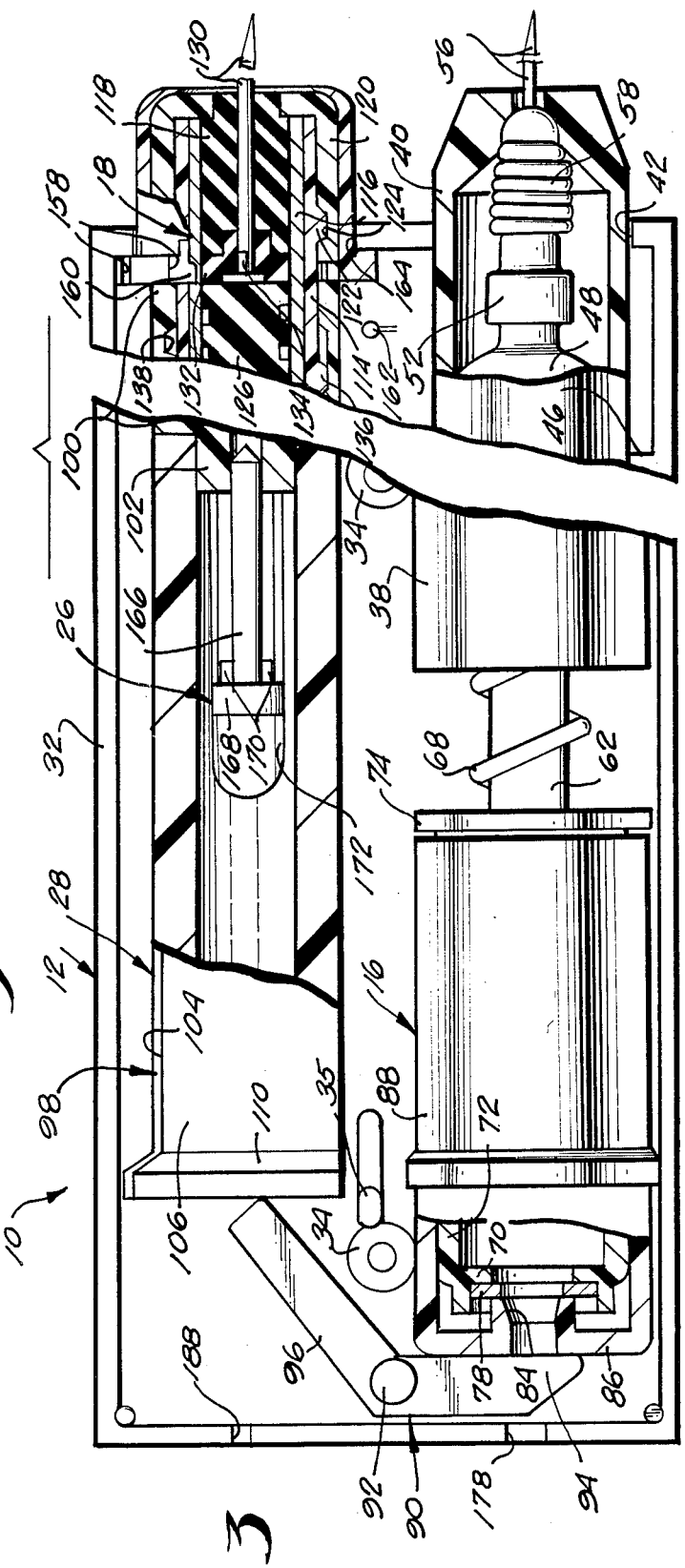

PLURAL DOSAGE AUTOMATIC INJECTOR WITH IMPROVED SAFETY

This invention relates to plural dose automatic injectors and more particularly to improvements in plural dose automatic injectors of the type disclosed in commonly assigned U.S. Pat. No. 4,226,235.

In addition to the above mentioned patent, reference is also made to commonly assigned U.S. Pat. No. 4,329,988. As disclosed in these two patents, one example of the need for the use of plural dose automatic injectors is presented in connection with situations which may arise in chemical warfare. In many situations now presented it has become necessary to provide military personnel with the capability of self-injecting a plurality of separate medicament dosages as, for example, 2 mg. of atropine and 600 mg. of pralidoxime chloride.

U.S. Pat. No. 4,329,988 discloses a plural injection assembly which includes a small dosage (atropine) automatic injector constructed in accordance with U.S. Pat. No. 2,832,339 and a relatively large dosage (pralidoxime chloride) automatic injector constructed in accordance with the disclosures contained in U.S. Pat. Nos. 3,712,301, 3,882,863 and 4,031,893. The assembly further includes a holder for stably supporting the separate automatic injectors together and for manually facilitating the sequential actuation thereof.

The specification and drawings contained in the U.S. Pat. No. 4,226,235 disclose several different embodiments of unitized plural injecting devices each of which includes first and second medicament injecting assemblies and first and second releasable stressed spring assemblies for operating the respective medicament injecting assemblies. In addition, means is provided for insuring that when one of the releasable stressed spring assemblies is actuated to operate the associated medicament injecting assembly, the other releasable stressed spring assembly will be actuated to operate the other medicament injecting assembly.

The embodiment illustrated in FIGS. 7 and 8 utilizes as the first and second medicament injecting and stressed spring assembly components of the device, the relatively large dosage automatic injector and relatively small dosage automatic injector included in the assembly of U.S. Pat. No. 4,329,988. In the embodiment illustrated in FIGS. 7 and 8 the large dosage injector component is actuated first and the small dosage injector component is actuated second in response to the actuation of the large dosage injector component. This actuation is accomplished by providing the small dosage injector with a separate stressed spring actuator which is held in stressed actuating position within the plural injector housing at a position rearwardly of the small dosage injector component. The stressed spring actuator is retained in stressed condition and released therefrom by engagement of one end of an actuating lever which extends forwardly between the large dosage injector component and the small dosage injector component within the housing to a position adjacent the forward end wherein the lever includes an arm disposed in a position to be moved by the forward movement of a housing member of the large dosage injector component when the latter is actuated. The provision of a separate stressed spring actuator for the small dosage injector component within the housing as well as the somewhat extended actuating lever unduly complicated the overall assembly and particularly rendered the safety means difficult to handle during assembly.

It is an object of the present invention to provide a plural dosage automatic injector which will obviate the problems noted above with respect to the embodiment illustrated in FIGS. 7 and 8 of U.S. Pat. No. 4,226,235.

In accordance with the principles of the present invention this objective is accomplished by providing the second releasable means of the second stressed spring assembly with an automatic safety means operable (1) when in a safety position with respect to the second releasable means to prevent actuation thereof, and (2) when removed from the safety position in relation to the second releasable means to permit the actuation of the second releasable means and mechanical motion transmitting means operable to transmit movement occurring as a result of actuation of the first releasable means into a secondary actuating movement operable to (1) effect a relative movement between the automatic safety means and the second releasable means sufficient to remove the automatic safety means from its safety position and (2) thereafter actuate the second releasable means to release the second stressed spring assembly to operate the second medicament injecting assembly.

Preferably, the manually operable safety means includes, in addition to the first safety means associated with the first releasable means, a second safety means operable (1) when in a safety position with respect to the mechanical motion transmitting means to prevent the latter from transmitting a secondary actuating movement, and (2) when removed from its safety position with respect to the mechanical motion transmitting means to permit the latter to transmit a secondary actuating movement. The second safety means prevents the mechanical motion transmitting means from transmitting a secondary actuating movement under conditions other than when the first stressed spring assembly is actuated, as, for example, in the event that the injector should be dropped in such a way that the force of the impact would result in the relative movement of the first medicament injecting assembly and first stressed spring assembly rearwardly within the housing assembly.

Preferably, the manually operable safety means includes a cap member having the first and second safety pins fixed thereto, the first safety pin being formed separately from the cap member so as to be capable of being initially disposed in its safety position with respect to the first releasable means prior to the mounting of the cap member on the housing assembly and means, such as a threaded fastener, operable to fixedly secure the cap member and the first safety pin together with the latter in its safety position when the cap member is mounted on the housing assembly.

Preferably, the mechanical motion transmitting means is in the form of a lever having relatively short arms and pivoted within the rearward portion of the housing assembly so as to transmit a rearward movement of a component of the first stressed spring assembly when actuated to an actuating member operatively associated with the second safety pin, the automatic safety means and the second stressed spring assembly.

Another object of the present invention is the provision of a plural dose automatic injector of the type described which is simple in construction, effective in operation and economical to manufacture.

These and other objects of the present invention will become more apparent during the course of the following detailed description and appended claims.

The invention may best be understood with reference to the accompanying drawings wherein an illustrative embodiment is shown.

In the drawings:

FIG. 1 is a top plan view of a plural dose automatic injector embodying the principles of the present invention showing the same with certain parts broken away for purposes of clearer illustration and with one-half of the housing assembly removed;

FIG. 2 is a sectional view taken along the line 2—2 of FIG. 1 illustrating the same as if all of the parts were present in FIG. 1;

FIG. 3 is a fragmentary view similar to FIG. 1 illustrating the position of the parts after actuation has occurred, and FIG. 4 is a cross-sectional view taken along the line 4—4 illustrating the same as if all of the parts were present in FIG. 1.

Referring now more particularly to the drawings there is shown therein a plural dosage automatic injector, generally indicated at 10, which embodies the principles of the present invention. The injector 10 includes, in general, a housing assembly, generally indicated at 12, a first or large dosage medicament injecting assembly, generally indicated at 14, mounted within the forward end portion of the housing assembly, and a first stressed spring assembly, generally indicated at 16, within the rearward end portion of the housing assembly 12, disposed in operating relation with the latter. Mounted in the forward portion of the housing assembly 12 alongside the first medicament injecting assembly 14 is a second or small dosage medicament injecting assembly, generally indicated at 18. Mounted within the housing assembly 12 rearwardly of the medicament injecting assembly 18 is a second stressed spring assembly 20 for operating the medicament injecting assembly 18. Mounted on the rearward end portion of the housing structure 12 is a manually operable safety assembly, generally indicated at 122, which includes a first safety pin means, generally indicated at 24, operatively associated with the first stressed spring assembly 16. An automatic safety means, generally indicated at 26, is provided within the housing assembly 12 in operative relation with the second stressed spring assembly 20. Finally, a mechanical motion transmitting mechanism, generally indicated at 28, is mounted in operative relation with respect to the first stressed spring assembly 16 and the second stressed spring assembly 20 so as to transmit a movement occurring as a result of the release of the first stressed spring assembly 16 into a secondary actuating movement operable to remove the automatic safety means from operative relation with the second stressed spring assembly 20 and to thereafter effect the release of the latter.

The housing assembly 12 includes a pair of outer housing members 30 and 32 which are configured as two component halves of a hollow generally tubular housing structure. As best shown in FIG. 2, the central interior of each housing member is formed with a series of spaced bosses 34 for receiving a series of fasteners 36 which serve to detachably fixedly secure the outer housing members 30 and 32 together. Bosses 34 are reinforced by triangular abutments 35 which engage one another when the fasteners are cinched down. The housing assembly 12 also includes a cylindrical tubular housing member 38 within which the first medicament injecting assembly 14 is mounted. As best shown in FIG. 1, the housing member 38 includes a forward end portion 40 of reduced diameter which extends forwardly through a forward opening 42 in the cooperating outer housing members 30 and 32 and constitutes a forward end of the housing assembly 12 which is adapted to engage the patient.

The reduced forward end portion 40 of the housing member 38 defines a forwardly facing annular shoulder 44 which abuts against the rearward surface of a pair of semicircular ridges 46 formed interiorly within the outer housing members 30 and 32 in rearwardly spaced relation with respect to the opening 42. Ridges 46 thus positively prevent forward movement of the housing member 38 within the housing members 30 and 32.

As best shown in FIG. 1, the large dosage medicament injecting assembly 14 includes a cylindrical container 48 of glass or plastic the rearward end of which is open and has a plunger 50 slidably mounted therein. The forward end of the container 48 is necked down and flanged to fixably receive a hub 52. Hub 52 is preferably constructed in accordance with the teachings contained in U.S. Pat. No. 3,380,449 (see also U.S. Pat. Nos. 3,391,695 and 3,424,155) so as to contain a burstable diaphragm (not shown) which serves to seal a liquid medicament dosage 54 within the container forwardly of the plunger 50 from normal contact with a hypodermic needle 56 fixedly supported by the hub 52 and extending forwardly therefrom. A rubber sheath 58 encompasses the exterior of the needle 56 so as to maintain the same in a sterile condition. As shown, a spacer 60 is connected with the plunger 50 so as to fill the rearward end of the container. In this regard see U.S. Pat. No. 4,031,893 the disclosure of which is hereby incorporated by reference into the present specification, together with the disclosures of U.S. Pat. Nos. 2,832,339, 3,380,449, 3,391,695, 3,424,155, 3,712,301, 3,797,489, 3,882,863, 4,225,235 and 4,329,988 previously discussed.

The stressed spring assembly 16 includes an inner collet member 62 made up of two interfitted stampings providing shoulders 64 on the forward ends thereof for engaging the rearward surface of the spacer 60. Spacer connecting barbs 66 extend forwardly from the inner member 62 in connecting relation with the spacer 60. A coil spring 68 is disposed around the inner member 62 and its forward end engages the rearward surface of the shoulders 64. The spring 68 is placed under stress by compressing rearward the end of the spring 68 in engagement with the forward surface of an apertured rear wall 70 of a tubular member 72 which extends forwardly in surrounding relation to the exterior of the coil spring 68, and has its forward extremity exteriorly flanged, as indicated at 74, to engage the rear end of housing member 38. The rearward end portions of the stampings of the inner member 62 are tapered rearwardly and split to define four releasable spring fingers 76 which extend through the aperture in the rear wall 70 and through an apertured locking ring 78 carried on the rearward surface of the rear wall 70. Spring fingers 76 include forwardly facing locking surfaces 80 engagable with the locking ring 78 and rearwardly and outwardly facing cam release surfaces 82. Cam surfaces 82 are adapted to engage a mating forwardly and inwardly facing frustoconical cam release surface 84 formed on the interior of an aperture rear wall 86 of an outer cylindrical member 88 slidably surrounding the exterior periphery of the cylindrical member 72.

The outer cylindrical member 88 is normally held within the housing assembly 12 against rearward movement by the motion transmitting mechanism 28. As shown, the motion transmitting mechanism includes a bell crank lever, generally indicated at 90, molded of plastic material and having opposed central shaft portions 92 pivotally received within a suitable aperture and recess formed in the outer housing members 30 and 32 respectively. The bell crank lever 90 includes a first lever arm 94 which extends forwardly and outwardly from the central shaft portion 92 so that the outer end thereof engages the rearward surface of the apertured end wall 86 of the outer housing member 88, and a second lever arm 96 extending transversely outwardly from the shaft portions 92 in a direction opposite from the direction of outward extension of the lever arm 94.

Lever arm 96 is normally disposed in engagement with the rearward surface of a tubular actuating member, generally indicated at 98, which, like the bell crank lever 90, is molded of plastic material and constitutes the second component of the motion transmitting mechanism 28. The forward end of the tubular actuating member 98 engages the rearward surface of a cylindrical housing member 100 within which the small dosage medicament injecting assembly 18 and second stressed spring assembly 20 are mounted. As shown, the housing member 100 includes a rearward cylindrical projecting portion 102 of reduced exterior diameter slightly more than the interior diameter of the tubular actuating member 98 so as to snugly engage therein and retain the actuating member 98 in axial alignment with the housing member 100. The rearward end portion of the actuating member 98 is formed with a transverse slot 104 in the half thereof corresponding with the half of the housing assembly defined by the outer housing member 30 so as to define therein an integral outer spring finger 106. The other half of the rearward end portion of the actuating member is provided at its rearward extremities with an outer peripheral guide flange 108 which engages the adjacent interior of the outer housing member 32. A similar flange providing a forwardly and outwardly facing releasable locking surface 110 is formed on the extremity of the spring finger 106. As best shown in FIG. 4, formed integrally on the adjacent interior of the outer housing member 30 is a portion providing a cooperating rearwardly and inwardly facing locking surface 112.

The housing member 100 forms the exterior housing part of a single small dosage automatic injector such as disclosed in U.S. Pat. No. 2,832,339. As shown, the injector includes an inner cylindrical housing member 114 within the housing member 100 within which is mounted the medicament injecting assembly 18 and the stressed spring assembly 20. The forward portion of the inner housing member 114 is formed with a counterbore for receiving therein a cylindrical dosage container 116. The forward end of the container is closed by a stopper or plug 118 of suitable rubber or plastic material. Plug 118 is retained in closing relation with the forward end of the container 116 by a housing end cap member 120 of molded plastic material. The cap is retained on the inner housing member 114 by interengagement of a pair of ridges 112 formed on the exterior periphery of the tubular member 114 with an annular groove 124 formed on the interior periphery of the cap member 120.

The rearward end of the dosage container 116 is closed by a plunger 126 which is slidably sealingly engaged within the rearward end thereof so as to enclose within the container a dosage 128 of a liquid medicament. A hypodermic needle 130 is disposed within the container 116 and has its pointed end disposed within a recess formed in the plug 118. A disk 132 of plastic is disposed within the forward end of the container 116 in surrounding sealed relation with the hypodermic needle 130 and in abutting engagement with the plug 118. The disk serves to releasably hold the needle in its storage position and to provide peripheral sealing therefor during the dosage injecting stroke of the plunger 126. The opposite end of the hypodermic needle 130 is enlarged for engagement by the plunger and has a slot 134 formed in its periphery adjacent the enlarged end for communicating the dosage 128 with the hollow interior of the hypodermic needle 130 when the plunger 126 is in engagement therewith. The inner housing member 114 is mounted within the outer housing member 100 for limited reciprocating movement as determined by a pair of ridges 136 formed on the exterior periphery of the tubular inner housing member 114 at a position spaced rearwardly from the annular ridge 122. The pair of ridges 136 is adapted to engage within an elongated annular groove 138 formed on the interior periphery of the outer housing member 100.

The stressed spring assembly 20 includes an elongated collet member 140 made up of two interfitted stampings, similar to the collet member 62, collet member 140 is disposed within the rearward end portion of the housing member 114 and has its forward end disposed in abutment with the plunger 126. The forward end of the collet member 140 is also exteriorly configured to engage the forward end of a stressed coil spring 142 which surrounds the central portion of the elongated member 140 within the inner housing member 114 and has its rearward end engaged with an apertured end wall 144 formed integrally on the rearward end of the inner housing member 114.

The rearward ends of the stampings of the elongated member 140 are split to provide four laterally movable spring fingers 146, the rearward extremities of which are formed with rearwardly and outwardly facing cam releasing surfaces 148. Extending inwardly from the forward end of each cam surface 148 is a locking shoulder 150 adapted to engage a locking ring 152 seated on the rear surface of the centrally apertured rear wall 144. The forward portion of the cylindrical projection 102 is formed with a frustoconical cam surface 152 which is disposed in engagement with the cam surfaces 148 so as to effect a laterally inward movement of the spring fingers toward one another to disengage locking shoulders 150 from locking ring 152 in response to a relative forward movement of the outer housing member 100 with respect to the inner housing member 114.

This relatively forward actuating movement of the housing member 100 comes at the end of a secondary actuating movement transmitted thereto through the motion transmitting mechanism 28 from a movement resulting from the release of the first stressed spring assembly 16. During the first part of this secondary actuating movement, the entire small dosage automatic injector unit as described above is moved forwardly as a unit within the outer housing structure provided by the outer housing members 30 and 32. In order to stably support the entire unit within the outer housing structure in a position to permit the aforesaid unitary forward movement, a flanged support cap member 156 is mounted over the cap member 120. The flange of the cap member 156 is formed with a pair of parallel slots 158 at each of two diametrically disposed positions. Each pair of slots 158 defines a spring locking tab having an inner locking surface 160 which engages over the adjacent rearward surface of the cap member 120.

As best shown in FIGS. 1 and 2, the forward inward portion of the flange of the support cap member 156 is adapted to engage a pair of releasable support pins 162 formed integrally on the adjacent interior of the outer housing members 30 and 32. It will be noted that the forward end wall provided by the cooperating housing members 30 and 32 provides an opening 164 through which the support cap member 156 partially extends when the flange is engaged by the releasable support pins 162. During the initial portion of the secondary actuating movement when the small dosage automatic injector is being moved forwardly as a unit, support pins 162 bend and give way releasing the support cap member 156 to advance with the unit until the flange thereof engages the rearwardly facing surface of the housing structure defining the opening 164.

The entire initial portion of the secondary actuating movement when the cap member 156 moves forwardly with the automatic injector unit also serves to remove the automatic safety means 26 from its normal safety position. As shown, the automatic safety means 26 includes a forward pin portion 166, which, when the safety means 26 is in its normal safety position, extends forwardly through the central aperture in the housing portion 102 and between the spring fingers 146 of the member 140 forwardly of the apertured rear wall 144 of the inner housing member 114. The pin portion 166 when in this safety position positively prevents the inward movement of the spring fingers 146 insuring that locking surfaces 150 are retained in engagement with locking ring 152.

Formed on the rearward end of the pin portion 166 in rearwardly spaced relation to the housing portion 102 when the automatic safety means 26 is in its safety position is an enlarged pin removal portion 168. The forward surface of enlarged portion 168 is adapted to be engaged by an abutment member 170 formed integrally on the adjacent interior of the outer housing member 32 and entending through an axially elongated slot 172 formed in the adjacent forward end portion of the actuating member 98. To further stabilize the support of the actuating member 98 within the outer housing structure in its normal position while at the same time permitting a forward secondary actuating movement thereof, there is formed integrally on the interior of the outer housing member 32 at a position adjacent the rearward end of the slot 172 a releasable pin 174.

The manually operable safety means includes a first safety means in the form of separate safety pin 176 which, when disposed in a normal safety position with respect to the first stressed spring assembly 16, extends forwardly through the central aperture in the end wall 86 and between the spring fingers 76 forwardly of the apertured end wall 70 so as to prevent the spring fingers 76 from moving laterally inwardly thus retaining locking surfaces 80 in engagement with locking ring or disk 78. The safety pin 176 also extends rearwardly through an opening 178 formed in the adjacent rear wall portion of the outer housing members 30 and 32 and has a flanged rearward end 180 disposed exteriorly of the outer housing structure.

The manually operable safety means 22 also includes a flanged cap member 182 which is shaped to fit over the rearward end portion of the outer housing members 30 and 32 when they are secured together. A threaded fastener 184 extending through the cap member 182 and into the pin 76 serves to fixedly secure the latter to the cap member so that the pin 176 will be removed from its safety position when the cap member is manually removed from its normal position over the rearward end portion of the housing assembly 12.

Formed integrally with the cap member 182 is a second safety means in the form of a forwardly extending pin portion 186. In the normal safety position of the pin portion 186, the same extends forwardly through an appropriate opening 188 in the adjacent rear wall portions of the outer housing members 30 and 32 past the lever arm 96 and into the slot 104 of the actuating member 98. The presence of the pin portion 186 within the slot 104 prevents spring finger 106 from moving laterally inwardly so as to insure that surface 110 will remain in engagement with surface 112. The presence of pin portion 186 within slot 104 also prevents the actuating member 98 from transmitting a secondary actuating movement under conditions other than when the first stressed spring assembly is actuated, as, for example, in the event that the injector 10 should be dropped in such a way that the force of the impact would result in the relative movement of the first medicament injecting assembly 14 and first stressed spring assembly 16 rearwardly within the housing assembly 12.

It is important to note that the construction of the automatic safety means 26 and separate nature of the first safety pin 176 of the manually operable safety means 22 enables the associated stressed spring assemblies 20 and 16 to be separately assembled and handled in the usual way in which they are handled in assembling the small dosage automatic injector as a unit or the two assembly components 14 and 16 of the conventional large dosage automatic injector unit. The entire injector 10 of the present invention is assembled by mounting the two component assemblies 14 and 16 with the safety pin 176 in its safety position within the housing member 32. The small dosage automatic injector unit in its normally assembled condition with the safety pin 166 in its safety position has its rearward end fitted with the actuating member 98 and its forward end fitted with the cap member 156. This sub-assembly is then mounted within the outer housing member 32 taking care to insure that the abutment 170 is properly positioned through the slot 172 forwardly of the pin portion 168 and that pins 162 and 174 are properly located, (pin 174 extends through slot 172 as shown) the bell crank lever 90 is then moved into its operative position (or has been positioned therein previously). The other outer housing member 30 is then positioned in proper relationship over the interior components mounted in the housing member 32 so as to register with the outer housing member 32. Bolts 36 are then secured in position to retain the two outer housing members 30 and 32 in their operative position. Finally, safety cap member 182 is fitted over the rearward end portion of the housing assembly 12 and threaded fastener 184 is extended therethrough and engaged within the rear end 180 of the safety pin 176.

When it is desired to actuate the injector 10, the user manually grips the exterior of the housing assembly 12 and then removes the manually operable safety means 22 by gripping the safety cap member 182 and moving it rearwardly. Next, the user moves the forward end of the member 40 into engagement with the thigh so that a continued force applied to the exterior of the housing assembly 12 causes the cam surfaces 82 of the spring fingers 76 to move rearwardly with respect to the cam surface 84 which causes the spring fingers 76 to move laterally inwardly and hence the locking surfaces 80 to move out of engagement with the locking ring 78.

It will be noted that the releasable pin 174 insures that this initial manual actuation will take place by providing a resistance to the movement of the first stressed spring assembly 16 as a unit in motion transmitting relation with the bell crank lever 90 which, in the absence of the resistance provided by the releasable pin 174, could result in the movement of the actuating member 98 through a secondary actuating movement without there being an actuating movement of the first stressed spring assembly 16. Pin 174 thus insures that the outer member 88 containing the releasing cam surface 84 will be held against movement (for release later) while the continue.d manual pushing force acting on the forward end of the member 40 is transmitted to the spring fingers 76 to effect their release. In this regard it will be noted that prior to actuation, the forward end of the member 40 is disposed forwardly of the housing assembly 12 to a greater extent than the forward end of support cap member 156 thereby enhancing the users ability to operate the plural dosage injector 10 with an actuating force equal to that normally applied to a comparable single dosage injector. The presence of automatic safety pin portion 166 in its safety position at all times prior to the actuation of the first stressed spring assembly 16 as aforesaid insures that the second stressed spring assembly 20 cannot be accidently actuated by itself as by an unwanted application of force to the forward end of the cap member 156 or the like.

As soon as the locking surfaces 80 are released from the locking ring 70 stressed spring 68 causes the member 62 to move forwardly and the members 72 and 88 to move together rearwardly. The forward movement of the member 62 causes the container 48 to move forwardly carrying with it the needle 56 which pierces through the end of the sheath 58, the plunger 50 continues to move forwardly with the member 62 thus forcing the dosage 54 of liquid medicament within the container 48 outwardly thereof through the needle 56 and into the patient.

Simultaneously, with the forward movement of the member 62, the rearward movement of the members 72 and 88 cause the lever arm 94 of the bell crank lever 90 to move rearwardly and effect a corresponding clockwise movement of the bell crank lever 90, as viewed in FIG. 1. This clockwise pivotal movement of the bell crank lever 90 causes the lever arm 96 to move forwardly, which movement is transmitted through the actuating member 98 into a secondary actuating movement for the assemblies 18 and 20. During the initial portion of the secondary actuating movement, pins 174 and 162 are bent over to allow the actuating member 98 and the entire small dosage automatic injector as a unit together with the support cap member 156 forwardly for a distance sufficient to move the spring fingers 146 forwardly of the forward end of the safety pin 166. At this point automatic safety means 26 has been removed from its safety position. Since the safety pin 166 has been removed from its safety position, the continued movement of the actuating member 98 through the last part of its secondary actuating movement has the effect of moving the outer housing member 100 forwardly with respect to the inner housing member 114 during which cam surface 154 on the outer housing member 100 engage the cam surfaces 148 of the spring fingers 146 and cause the latter to move inwardly toward one another to an extend sufficient to disengage the locking surfaces 150 thereof from the locking ring 152. When this release occurs, stressed spring 142 moves the member 140 forwardly which has the effect of moving plunger 126 forwardly within the container 116. The movement of the plunger 126 carries with it the needle 130 which pierces through the plug 118 and into the muscle tissue of the patient alongside the position of the needle 56. Simultaneously, with the movement of the needle into the patient, the dosage 128 of liquid medicament is forced outwardly of the container 116 through the slot 134 of the needle and, finally, outwardly of the pointed end thereof into the muscle tissue of the patient with the needle. After the medicament dosages have been injected as indicated above, the user need only move the housing assembly rearwardly away from the position of injection to withdraw the needles 56 and 130.

It thus will be seen that the objects of this invention have been fully and effectively accomplished. It will be realized, however, that the foregoing preferred specific embodiment has been shown and described for the purpose of illustrating the function and structural principles of this invention and is subject to change without departure from such principles. Therefore, this invention includes all modifications encompassed within the spirit and scope of the following claims.

What is claimed is:

1. In a plural hypodermic needle and plural spring actuated injecting device of the type comprising outer housing means adapted to be exteriorly manually engaged by a user, a first cylindrical liquid container within said outer housing means, a first hypodermic needle disposed within said outer housing means in a storage position in operative association with said first container, first plunger means operatively associated with said first container, first spring means operatively associated with said first plunger means within said outer housing means, first releasable means normally retaining said first spring means in a stressed condition within said outer housing means, operable upon actuation in response to a predetermined manual actuating procedure to effect release of the stressed condition of said first spring means so that the spring force resulting from said release acts upon said first plunger means to move (1) said first hypodermic needle from said storage position to an extended position into the user and (2) liquid within said first container outwardly through said first hypodermic needle into the user; a second cylindrical liquid container, a second hypodermic needle operatively associated with said second liquid container, second plunger means operatively associated with said second liquid container, second spring means operatively associated with said second plunger means, second releasable means normally retaining said second spring means in a stressed condition operable upon actuation to effect release of the stressed condition of said second spring means, manually operable safety means including first safety means operable (1) when in a safety position with respect to said first releasable means to prevent actuation thereof as aforesaid and (2) when removed from said safety position in relation to said first releasable means to permit the actuation of said first releasable means as aforesaid, the improvement which comprises automatic safety means operable (1) when in a safety position with respect to said second releasable means to prevent actuation thereof as aforesaid and (2) when removed from said safety position in relation to said second releasable means to permit the actuation of said second releasable means as aforesaid, and mechanical motion transmitting means operable to transmit a movement occurring as a result of the actuation of said first releasable means into a secondary actuating movement operable to (1) effect a relative movement between said automatic safety means and said second releasable means sufficient to remove said automatic safety means from said safety position and (2) thereafter actuate said second releasable means to insure that the spring force resulting from the release of said second spring means by said second releasable means acts upon said second plunger means to move (a) said second hypodermic needle longitudinally outwardly into an extended position into the user in generally side-by-side relation to said first hypodermic needle and (b) liquid within said second container outwardly through said second hypodermic needle into said user.

2. The improvement as defined in claim 1 wherein said manually operable safety means includes second safety means operable (1) when in a safety position with respect to said motion transmitting means to prevent the latter from transmitting a secondary actuating movement and (2) when removed from said safety position with respect to said motion transmitting means to permit the latter to transmit a secondary actuating movement.

3. The improvement as defined in claim 2 wherein said manually operable safety means includes a cap member removably mounted on one end of said outer housing means opposite from an end thereof from which said needles extend when the latter are moved into said extended positions into the user;

said first and second safety means comprising parallel first and second safety pins fixed to said cap member.

4. The improvement as defined in claim 3 wherein said first safety pin is formed separately from said cap member so as to be operable to be initially disposed in said safety position with respect to said first releasable means prior to the mounting of said cap member on said outer housing means and means operable to fixedly secure said cap member and said first safety pin together with the latter in said safety position when said cap member is mounted on said one end of said outer housing means.

5. The improvement as defined in claim 4 wherein said securing means comprises a threaded fastener extending through said cap member and threadedly engaged with said first safety pin.

6. The improvement as defined in claim 3 wherein said second safety pin is integral with said cap member.

7. A plural dosage automatic injector comprising an elongated tubular housing assembly, a first medicament injecting assembly including a first container, a first hypodermic needle, a first liquid medicament and a first plunger within the forward end portion of said housing assembly, a first stressed spring assembly in the rearward end portion of said housing assembly disposed in operative relation with said first medicament injecting assembly for operating the latter so as to move the first plunger forwardly within the first container, the first needle forwardly into a patient, and the first liquid medicament outwardly of the first needle, said first stressed spring assembly including first releasable means operable upon actuation in response to the performance of a manual actuating procedure to release said first stressed spring assembly to operate said first medicament injection assembly, a second medicament injecting assembly including a container, a hypodermic needle, a liquid medicament and a plunger within the forward end portion of said housing assembly alongside said first medicament injecting assembly, a second stressed spring assembly in the rearward end portion of said housing assembly alongside said first stressed spring assembly disposed in operative relation with said second medicament injecting assembly for operating the latter so as to move the second plunger forwardly into a patient alongside said first needle and the second liquid medicament outwardly of the second needle, said second stressed spring assembly including second releasable means operable upon actuation to release said second stressed spring means to operate said second medicament injection assembly, manually operable safety means including first safety means operable (1) when in a safety position with respect to said first releasable means to prevent actuation thereof as aforesaid and (2) when removed from said safety position in relation to said first releasable means to permit the actuation of said first releasable means as aforesaid, automatic safety means operable (1) when in a safety position with respect to said second releasable means to prevent actuation thereof and (2) when removed from said safety position in relation to said second releasable means to permit the actuation of said second releasable means, and mechanical motion transmitting means operable to transmit a movement occurring as a result of the actuation of said first releasable means into a secondary actuating movement operable to (1) effect a relative movement between said automatic safety means and said second releasable means sufficient to remove said automatic safety means from said safety position and (2) thereafter actuate said second releasable means to release said second stressed spring assembly to operate said second medicament injecting assembly.

8. A plural dosage automatic injector as defined in claim 7 wherein said housing assembly includes a plurality of outer housing members defining an outer housing structure, an inner cylindrical housing member within which said second medicament assembly and said second stressed spring assembly is operatively mounted, a second cylindrical housing member mounted within said outer housing structure for forward movement from a normal position therein, means mounting said inner cylindrical housing member within said second cylindrical housing member for limited relative axial movement with a forward end portion thereof extending forwardly therefrom, and forward cap means on the forward end portion of said inner cylindrical housing member extending forwardly through said outer housing structure.

9. A plural dosage automatic injector as defined in claim 8 wherein said second releasable means is actuated by a relative forward axial movement of said second cylindrical member with respect to said inner cylindrical member when said automatic safety means is removed from said safety position, said motion transmitting means including an actuating member movable through a forward secondary actuating movement connected in forward motion transmitting relation with said second cylindrical member, said automatic safety means including an automatic safety pin extending rearwardly from said second cylindrical member when in said safety position and having an enlarged removal portion on the rearward end thereof, abutment means fixed with respect to said outer housing structure in an interior position to be engaged by said removal portion, and means stably supporting said inner cylindrical member and said forward cap means with respect to said outer housing structure such that upon the forward secondary movement of said actuating member said second cylindrical housing member, said inner cylindrical housing member and said forward cap means are moved forwardly therewith while said abutment means prevents forward movement of said automatic safety means until the latter is removed from said safety position and thereafter the forward movement of said forward cap means and said inner cylindrical housing member is arrested so that the continued forward movement of said second cylindrical housing member with said actuating member actuates said second releasable means.

10. A plural dosage automatic injector as defined in claim 9 wherein said mechanical motion transmitting means further includes a bell crank lever pivotally mounted within the rearward end portion of said housing assembly, said bell crank lever including a first forwardly extending lever arm, said first stressed spring means including a member disposed in rearward motion transmitting relation to the forward end of said first lever arm operable to be moved rearwardly in response to the actuation of said first releasable means, said bell crank lever having a second lever arm disposed in forward motion transmitting relation with said actuating member.

11. A plural dosage automatic injector as defined in claim 10 wherein said first medicament injecting assembly and said first stressed spring means are mounted in cooperating relation within said outer housing structure such that said first releasable means is actuated by the performance of a manual actuating procedure which includes the application of a forwardly directed manual gripping force on said outer housing structure while the forward end of said housing assembly is in engagement with a patient.

12. A plural dosage automatic injector as defined in claim 9 wherein said manually operable safety means includes a cap member removably mounted on the rearward end portion of said outer housing structure, said first safety means including a first safety pin formed separately from said cap member so as to be operable to be initially disposed in said safety position with respect to said first releasable means prior to the mounting of said cap member on said outer housing structure and means operable to fixedly secure said cap member and said first safety pin together with the latter in said safety position when said cap member is mounted on said one end of said outer housing structure.

13. A plural dosage automatic injector as defined in claim 12 wherein said actuating member includes a slot in the rearward end portion thereof defining an integral spring finger portion having a forwardly facing releasably locking surface normally engaged with a cooperating releasable locking surface fixed with respect to said outer housing structure, said manually operable safety means including a second safety pin integral with said safety cap member extending forwardly in a safety position within said actuating member slot.

14. A plural dosage automatic injector as defined in claim 9 wherein said forward cap means includes an inner cap member forming with said second cylindrical housing member, said inner cylindrical housing member and the second medicament injecting and stressed spring assemblies mounted therein a single small dosage unit, said forward cap members also including an outer cap member fitted over said inner cap member and having an exterior flange engagable with said stably supporting means.

15. A plural dosage automatic injector as defined in claim 14 wherein said stably supporting means includes releasable pin means integrally with the interior of said outer housing structure.

16. A plural dosage automatic injector as defined in claim 14 wherein said outer cap member includes a plurality of annular spaced pairs of peripheral slots, each pair of slots defining a spring finger portion for retaining said outer cap member in fitted relation over said inner cap member.

* * * * *